US012753142B2

(12) United States Patent
Yamauchi et al.

(10) Patent No.: US 12,753,142 B2
(45) Date of Patent: Oct. 6, 2026

(54) METHOD FOR PRODUCING (METH)ACRYLIC MONOMER

(71) Applicant: MICROWAVE CHEMICAL CO., LTD., Osaka (JP)

(72) Inventors: Tomohisa Yamauchi, Osaka (JP); Akiyori Hagimoto, Osaka (JP); Kiyoshi Tsunoda, Osaka (JP); Yukari Deguchi, Osaka (JP)

(73) Assignee: Microwave Chemical Co., Ltd., Osaka (JP)

( * ) Notice: Subject to any disclaimer, the term of this patent is extended or adjusted under 35 U.S.C. 154(b) by 485 days.

(21) Appl. No.: 18/562,198

(22) PCT Filed: May 20, 2022

(86) PCT No.: PCT/JP2022/021008
§ 371 (c)(1),
(2) Date: Nov. 17, 2023

(87) PCT Pub. No.: WO2022/244881
PCT Pub. Date: Nov. 24, 2022

(65) Prior Publication Data

US 2024/0217914 A1 Jul. 4, 2024

(30) Foreign Application Priority Data

May 20, 2021 (JP) ................................ 2021-085660

(51) Int. Cl.
*C07C 67/475* (2006.01)
*C08J 11/10* (2006.01)
*C08J 11/12* (2006.01)

(52) U.S. Cl.
CPC ............. *C07C 67/475* (2013.01); *C08J 11/10* (2013.01); *C08J 11/12* (2013.01); *C08J 2333/12* (2013.01)

(58) Field of Classification Search
CPC .......... C07C 67/475; C08J 11/10; C08J 11/12
See application file for complete search history.

(56) References Cited

U.S. PATENT DOCUMENTS 6,160,031 A 12/2000 Porée et al.
2009/0318579 A1 12/2009 Ikenaga
(Continued)

FOREIGN PATENT DOCUMENTS

JP 2000-516274 A 12/2000
JP 2006-232966 A 9/2006
(Continued)

OTHER PUBLICATIONS

Extended European Search Report for App. No. 22804788.2, dated Jul. 24, 2025 (in 8 pages).
(Continued)

*Primary Examiner* — Yate' K Cutliff
(74) *Attorney, Agent, or Firm* — Knobbe, Martens, Olson & Bear, LLP

(57) ABSTRACT

The purpose of the present invention is to provide a method for producing a (meth)acrylic monomer that suppresses heterogeneity of a (meth)acrylic resin depolymerization system and that makes it easier for microwaves to reach the system interior efficiently. According to this method for producing a (meth)acrylic monomer, which includes a step 1 for irradiating a prepared (meth)acrylic resin with microwaves and mixing to obtain a melt containing a (meth) acrylic resin having reduced molecular weight, a step 2 for adding additional (meth)acrylic resin to the melt and mixing to obtain a mixture containing additional (meth)acrylic resin in the melt, and a step 3 for irradiating the mixture with microwaves and mixing to obtain a (meth)acrylic monomer, it is possible to suppress heterogeneity of the (meth)acrylic
(Continued)

resin depolymerization system and to make it easier for microwaves to reach the system interior efficiently.

10 Claims, 1 Drawing Sheet

(56) References Cited

U.S. PATENT DOCUMENTS

| | | | | |
|---|---|---|---|---|
| 2021/0115216 | A1* | 4/2021 | Dubois | C08J 11/12 |
| 2021/0246243 | A1* | 8/2021 | Dubois | C08F 220/18 |

FOREIGN PATENT DOCUMENTS

| | | | |
|---|---|---|---|
| JP | 2007-230905 | A | 9/2007 |
| JP | 2010-174249 | A | 8/2010 |
| JP | 2010-185077 | A | 8/2010 |
| WO | WO 2019/207260 | A1 | 10/2019 |
| WO | WO 2019/207265 | A1 | 10/2019 |

OTHER PUBLICATIONS

International Search Report received in International Application No. PCT/JP2022/021008, mailed on Aug. 2, 2022.

* cited by examiner

METHOD FOR PRODUCING (METH)ACRYLIC MONOMER

TECHNICAL FIELD

The present invention relates to a method for producing a (meth)acrylic monomer. More specifically, the present invention relates to a technique for recovering a (meth) acrylic monomer from a (meth)acrylic resin.

BACKGROUND ART

An acrylic resin and a methacrylic resin (hereinafter, "acryl" and "methacryl" are collectively referred to as "(meth)acryl") are non-crystalline thermoplastic plastics having high transparency and impact resistance. Since the (meth)acrylic resin is easy to process and color, the (meth) acrylic resin is used in a wide range of use applications as a substitute for inorganic glass, such as light guide plates of a liquid crystal television and a liquid crystal display, a cover for a lighting fixture, a window material for buildings and vehicles, a motorcycle windshield, an aircraft canopy, a wristwatch windshield, and a water tank.

The production amount of the (meth)acrylic resin is expected to increase in the future. On the other hand, from the viewpoint of resource conservation, a technique of recycling a monomer by depolymerizing a (meth)acrylic resin to be discarded without producing a monomer from a fossil raw material has been studied.

For example, Patent Document 1 describes a method for decomposing a (meth)acrylic resin, the method including heating a solution in which a (meth)acrylic resin is dissolved to decompose the (meth)acrylic resin, in which the heating is performed while supplying an inert gas and/or water vapor into the solution, and specifically describes a method of flowing a heating medium by a jacket method, heating by an electric heater, and heating using a burner method by fuel combustion.

Patent Document 2 describes a method for recovering a (meth)acrylic acid ester, in which a resin-containing liquid obtained by dissolving or swelling a (meth)acrylic resin containing 50 mass % or more of a (meth)acrylic acid ester unit in a solvent having a boiling point of 250° C. or higher under atmospheric pressure is irradiated with microwaves to decompose the (meth)acrylic resin, and the obtained (meth) acrylic acid ester is separated.

PRIOR ART DOCUMENTS

Patent Documents

Patent Document 1: Japanese Patent Laid-open Publication No. 2006-232966

Patent Document 2: Japanese Patent Laid-open Publication No. 2007-230905

SUMMARY OF THE INVENTION

Problems to be Solved by the Invention

The technique described in Patent Document 1 requires a means for supplying a predetermined gas in addition to a heating means, and the equipment is complicated. The technique described in Patent Document 2 is a simple depolymerization system using microwaves as a heating means, but also requires the use of the solvent, and thus has a problem in that an undesirable by-product due to heating of the solvent is generated.

The (meth)acrylic resin has a low microwave-absorbing capability at room temperature, but has a property that the microwave-absorbing capability increases as the temperature increases. Since the microwave-absorbing capability is high near the depolymerization temperature (generally 280° C. or higher) of the (meth)acrylic resin, it can be originally expected that the (meth)acrylic resin is efficiently heated and decomposed by microwaves. Therefore, the present inventors have attempted depolymerization using a melting system of a raw material (meth)acrylic resin using microwaves as a heating means without using a solvent. However, the present inventors have actually studied, and as a result, have unexpectedly faced the problem that the property of the (meth)acrylic resin, which is originally advantageous in depolymerization, that is, has a high microwave absorbing capability, locally absorbs microwaves at the surface portion of the melt of the resin, so that the microwaves cannot penetrate deeply into the melt, and as a result, the microwaves hardly reach the (meth)acrylic resin inside, making uniform depolymerization difficult. These problems are more remarkable when the scale of the depolymerization system increases.

Therefore, an object of the present invention is to provide a method for producing a (meth)acrylic monomer capable of suppressing heterogeneity of a (meth)acrylic resin depolymerization system and efficiently promoting depolymerization in the entire melt.

Means for Solving the Problem

The present inventors have conducted intensive studies, and as a result, have found that by newly adding and mixing a (meth)acrylic resin from the outside of the system to a melt containing a component having a reduced microwave-absorbing capability obtained by microwave irradiation and mixing of a (meth)acrylic resin, and irradiating the (meth) acrylic resin with microwaves in a state of being dispersed in the melt, the heterogeneity of the depolymerization system of the (meth)acrylic resin is suppressed and microwaves are easier to reach the system interior efficiently. The present inventors have conducted further studies based on the findings, leading to the completion of the present invention.

That is, the present invention provides inventions of the following aspects.

Item 1. A method for producing a (meth)acrylic monomer, the production method including:

- a step 1 for irradiating a charged (meth)acrylic resin with microwaves and mixing to obtain a melt containing a component having a microwave-absorbing capability lower than a microwave-absorbing capability of the charged (meth)acrylic resin at a depolymerization temperature:
- a step 2 for adding an additional (meth)acrylic resin to the melt and mixing to obtain a melt mixture containing the additional (meth)acrylic resin in the melt; and
- a step 3 for irradiating the melt mixture with microwaves and mixing to obtain a (meth)acrylic monomer.

Item 2. The production method described in Item 1, in which in the step 1, a charged amount of the charged (meth)acrylic resin is 2.5 kg or more.

Item 3. The production method described in Item 1 or 2, in which in the step 1, a charged amount of the charged (meth)acrylic resin is 80 kg or more.

Item 4. The production method described in any one of Items 1 to 3, in which the step 2 and the step 3 are repeated.

Item 5. The production method described in any one of Items 1 to 4, in which in the step 2, the additional (meth)acrylic resin does not have a thermal history of being provided at a depolymerization temperature.

Item 6. The production method described in any one of Items 1 to 5, in which in the step 2, an added amount of the additional (meth)acrylic resin is 5 to 20 parts by weight per 100 parts by weight of the charged amount of the charged (meth)acrylic resin.

Item 7. The production method described in any one of Items 1 to 6, in which in the step 2, the additional (meth)acrylic resin is added at a timing when the charged amount of the charged (meth)acrylic resin is reduced by 1 to 20 parts by weight from 100 parts by weight of the charged amount of the charged (meth)acrylic resin.

Item 8. The production method described in any one of Items 1 to 7, in which the step 3 is performed under a temperature condition of 300 to 360° C.

Item 9. The production method described in any one of Items 1 to 8, in which a frequency of the microwaves is 0.8 to 6 GHz.

Item 10. The production method described in any one of Items 1 to 9, in which the steps 1 to 3 are performed in a container having a bottom whose side wall has an inverted conical shape.

Advantages of the Invention

According to the present invention, there is provided a method for producing a (meth)acrylic monomer that suppresses heterogeneity of a (meth)acrylic resin depolymerization system and that makes it easier for microwaves to reach the system interior efficiently.

EMBODIMENTS OF THE INVENTION

1. Basic Process

Figure 1:
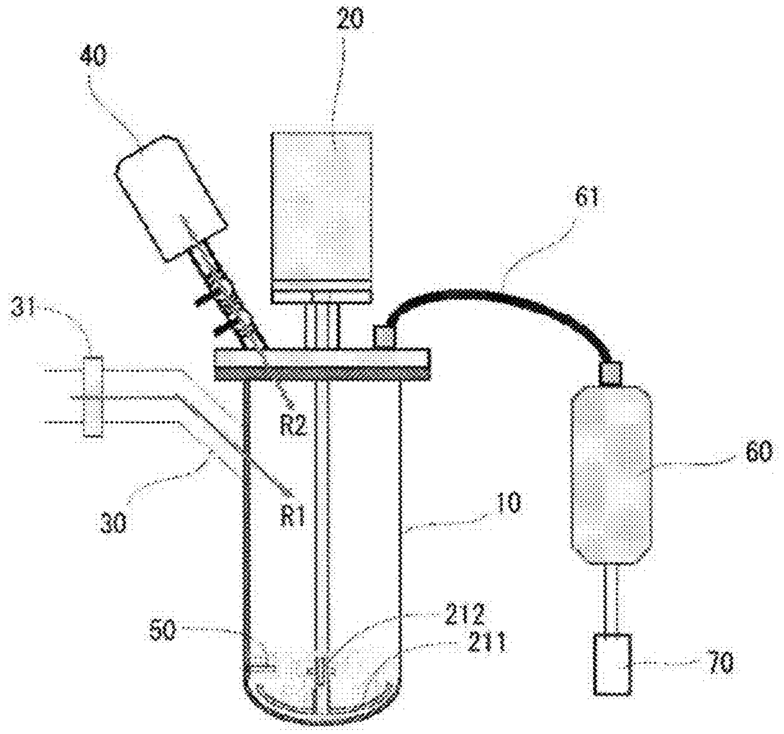
FIG. 1 is a schematic view of an example of a device used in a method for producing a (meth)acrylic monomer of the present invention.

A method for producing a (meth)acrylic monomer of the present invention includes a step 1 for irradiating a charged (meth)acrylic resin with microwaves and mixing to obtain a melt containing a component having a microwave-absorbing capability lower than a microwave-absorbing capability of the charged (meth)acrylic resin at a depolymerization temperature, a step 2 for adding an additional (meth)acrylic resin to the melt and mixing to obtain a melt mixture containing the additional (meth)acrylic resin in the melt, and a step 3 for irradiating the melt mixture with microwaves and mixing to obtain a (meth)acrylic monomer.

The step 2 is performed after the step 1, and the step 3 is performed after the step 2. The step 2 can be carried out without or with irradiation of microwaves, and is preferably carried out with irradiation of microwaves. The additional (meth)acrylic resin added in the step 2 is depolymerized into a low-molecular-weight (meth)acrylic resin (a (meth)acrylic resin having a molecular weight smaller than that of the additional (meth)acrylic resin) in the melt with a time difference from the charged (meth)acrylic resin prepared in the step 1, and with the progress of the depolymerization, the additional (meth)acrylic resin is decomposed to a (meth)acrylic monomer.

The step 2 and the step 3 are preferably repeated. In the repetition of the step 2 and the step 3, for example, a melt mixture to which an additional (meth)acrylic resin is added is prepared in the previous step 2, and a melt mixture to which an additional (meth)acrylic resin is newly added is prepared in the subsequent step 2 while the additional (meth)acrylic resin is depolymerized into a low-molecular-weight (meth)acrylic resin and decomposed to a (meth)acrylic monomer with the progress of depolymerization. That is, in the repetition of the step 2 and the step 3, a state where the melt mixture containing the new (meth)acrylic resin is dispersed in the depolymerization system can be continuously updated.

In a particularly preferred embodiment of the present invention, a (meth)acrylic monomer can be obtained by allowing depolymerization to proceed while continuously or intermittently adding and mixing an additional (meth)acrylic resin to a melt containing a component having a low microwave-absorbing capability, which is obtained by irradiating a charged (meth)acrylic resin with microwaves and mixing, while irradiating the additional (meth)acrylic resin with microwaves and mixing.

The depolymerization system used in the production method of the present invention is usually in a sealed state, and the monomer as a product is in the form of a gas. The produced monomer is liquefied and recovered by a cooling device provided in communication with the depolymerization system atmosphere.

In one embodiment of the present invention, from the viewpoint of suppressing an increase in the amount of impurities in the recovered monomer, it is preferable not to further include a step for performing depolymerization without adding an additional (meth)acrylic resin and/or a step for performing depolymerization without stirring.

2. Step 1

In the step 1, a charged (meth)acrylic resin is irradiated with microwaves and mixed to obtain a melt containing a component having a microwave-absorbing capability lower than that of the charged (meth)acrylic resin at a depolymerization temperature.

In the step 1, the phrase "irradiating with microwaves and mixing" includes an aspect of mixing while irradiating with microwaves and an aspect of mixing after irradiating with microwaves.

The charged (meth)acrylic resin refers to a (meth)acrylic resin as a material to be first provided to the depolymerization system. A specific aspect of the (meth)acrylic resin is preferably a plastic material containing a (meth)acrylic resin, and more preferably a waste plastic material containing a (meth)acrylic resin. The charged (meth)acrylic resin may be input at one time, or may be input in plural times from the viewpoint of temperature uniformity of the entire charged (meth)acrylic resin, and the like. In the case of inputting the charged (meth)acrylic resin in plural times, when or until the charged (meth)acrylic resin input in first reaches the depolymerization system temperature, the remaining charged (meth)acrylic resin is input up to a target charged amount. For example, in the case of inputting the charged (meth)acrylic resin in two portions, when or until the charged (meth)acrylic resin input at the first time reaches the depolymerization system temperature, the remaining charged (meth)acrylic resin to be input at the second time is input. For example, in the case of inputting the charged (meth)acrylic resin in three or more portions, when or until the (meth)acrylic resin input at the first time reaches the depolymerization system temperature, the remaining charged (meth)acrylic resin is sequentially input up to a target charged amount, to a target charged amount, in plural times. Also in the case of inputting the remaining charged (meth)acrylic resin in plural times, when or until the entirety of the charged (meth)acrylic resin input at the first time and the charged (meth)acrylic resin input at the second and subsequent times reaches the depolymerization system temperature, the next charged (meth)acrylic resin is input.

Specific examples of the charged (meth)acrylic resin include polymers having a (meth)acrylic monomer selected from the group consisting of acrylic acid, methacrylic acid, and esters thereof as a constituent unit. Examples of the acrylic acid ester include methyl acrylate, ethyl acrylate, propyl acrylate, and butyl acrylate, and examples of the methacrylic acid ester include methyl methacrylate, ethyl methacrylate, propyl methacrylate, and butyl methacrylate. The charged (meth)acrylic resin may contain a constituent unit derived from any one of the (meth)acrylic monomers alone, or may contain constituent units derived from two or more different (meth)acrylic monomers in combination.

The amount of the constituent unit derived from the (meth)acrylic monomer contained in the charged (meth) acrylic resin is preferably 70 wt % or more, more preferably 80 wt % or more, still more preferably 90 wt % or more, even more preferably 95 wt % or more, and most preferably 100 wt %. When the charged (meth)acrylic resin contains a constituent unit derived from another monomer other than the (meth)acrylic monomer, examples of the other monomer include monomers selected from the group consisting of maleic anhydride, styrene, α-methylstyrene, and acrylonitrile.

The weight average molecular weight of the charged (meth)acrylic resin is not particularly limited, and is, for example, 80,000 to 2,000,000 and preferably 100,000 to 2,000,000. The weight average molecular weight (Mw) is a value measured in terms of standard polystyrene by a gel permeation chromatography (GPC) method.

In the plastic material containing the charged (meth) acrylic resin, the blending ratio of the (meth)acrylic resin is not particularly limited, but is preferably 70 wt % or more, more preferably 80 wt % or more, still more preferably 90 wt % or more, and even more preferably 95 wt % or more. The proportion of the (meth)acrylic resin in the resin contained in the plastic material containing a (meth)acrylic resin is not particularly limited, but is preferably 70 wt % or more, more preferably 80 wt % or more, still more preferably 90 wt % or more, even more preferably 95 wt % or more, and most preferably 100 wt %. In the plastic material containing a (meth)acrylic resin, examples of the additive component that may be contained in addition to the resin include dyes, pigments, and inorganic fillers.

The charged amount of the charged (meth)acrylic resin is not particularly limited. On the other hand, in the production method of the present invention, since the depolymerization system can be heated with high uniformity to make it easier for microwaves to reach the system interior efficiently, the effect of the present invention can be favorably obtained even in a large-scale depolymerization system in which an original problem in that the heating of the depolymerization system tends to be uneven and the microwaves hardly reach the system interior becomes remarkable. From such a viewpoint, preferred examples of the charged amount of the charged (meth)acrylic resin in one embodiment of the present invention include 2.5 kg or more, 2.8 kg or more, kg or more, or 3.2 kg or more, more preferably more than 50 kg, still more preferably 80 kg or more, and even more preferably 100 kg or more. The upper limit of the charged amount of the charged (meth)acrylic resin in the present invention is not particularly limited, and is, for example, 2000 kg or less or 1000 kg or less. In the case of inputting the charged (meth)acrylic resin in plural times, the charged amount of the charged (meth)acrylic resin refers to the total amount (that is, the target charged amount) of the charged (meth) acrylic resin from the first time to the plural times. In the case of inputting the charged (meth)acrylic resin in plural times, a preferable charged amount is more than 50 kg. In this case, the input amount at the first time can be set to 50 kg or less, and then the remaining charged (meth)acrylic resin can be appropriately input up to the target charged amount.

By irradiating the charged (meth)acrylic resin with microwaves, when the resin is heated to be melted and reaches the depolymerization temperature, depolymerization partially proceeds at a position irradiated with microwaves, so that a low-molecular-weight (meth)acrylic resin (that is, a (meth) acrylic resin having a molecular weight smaller than that of the charged (meth)acrylic resin) is generated in the melt of the (meth)acrylic resin and dispersed in the melt by a mixing operation.

As the microwave irradiation output in the step 1, an output capable of heating the charged (meth)acrylic resin to a temperature at which the depolymerization proceeds is appropriately selected. The temperature at which the depolymerization of the (meth)acrylic resin proceeds in the step 2 is, for example, 280° C. or higher, specifically 300 to 390° C., preferably 320 to 390° C., more preferably 325 to 370° C., still more preferably 330 to 360° C., and even more preferably 335 to 350° C.

A specific irradiation output of the microwaves applied to the depolymerization system in the step 1 may be appropriately set according to the set temperature, the charged amount of the charged (meth)acrylic resin, and the like, and an effective output (a value obtained by subtracting a reflected wave (kW) from an incident wave (KW)) is, for example, 1 KW or more, preferably 1.2 KW or more, and more preferably 1.5 KW or more. The upper limit of the irradiation output (effective output) is not particularly limited, and is, for example, 200 kW or less.

The frequency of the microwaves applied to the depolymerization system in the step 1 is not particularly limited, and is, for example, 0.8 to 6 GHz. From the viewpoint of making it easier for microwaves to reach the inside of the melt, the frequency is preferably 0.8 to 2.5 GHZ, more preferably 0.8 to 1.5 GHZ, and still more preferably 0.8 to 1 GHz or 0.9 to 0.95 GHz. In the production method of the present invention, since the microwaves can reach the inside of the melt, the microwaves can reach the inside of the melt even when microwaves having a frequency of more than 2.5 GHz and 6 GHz or less or more than 1.5 GHZ and 6 GHz or less, particularly 4 to 6 GHz, which is inherently not advantageous in terms of deep penetration, are used.

The mixing method in the step 1 is not particularly limited, and examples thereof include a method of mixing with a stirrer, a method of rotating a container itself containing a melt, and a method of combining both of these methods. The degree of mixing may be a degree to which the composition of the melt becomes uniform.

The melt obtained in the step 1 contains a component having a microwave-absorbing capability lower than that of the charged (meth)acrylic resin at a depolymerization temperature. The component having a low microwave-absorbing capability is a component generated by irradiating the charged (meth)acrylic resin melt with microwaves, and is not specifically defined, but as a possibility, the above-described low-molecular-weight (meth)acrylic resin and/or a by-product (for example, a component that is not converted to the (meth)acrylic monomer but finally remains as a residue) other than the low-molecular-weight (meth) acrylic resin are considered. The presence of a component having a microwave-absorbing capability lower than that of the charged (meth)acrylic resin at a depolymerization temperature can be confirmed by measuring a real part of complex permittivity and an imaginary part of complex permittivity of each of the melt to be confirmed and the charged (meth)acrylic resin at the same temperature (provided that, the temperature is within the depolymerization temperature range), and calculating the power half-reduction depth of microwaves based on the measured values.

3. Step 2

In the step 2, an additional (meth)acrylic resin is added to and mixed with the melt obtained in the step 1 to obtain a melt mixture containing the additional (meth)acrylic resin in the melt.

In the step 2, the phrase "adding an additional (meth) acrylic resin and mixing" includes an aspect of mixing while adding an additional (meth)acrylic resin and an aspect of mixing after adding an additional (meth)acrylic resin.

Since the melt obtained in the step 1 contains a component having a microwave-absorbing capability lower than that of the charged (meth)acrylic resin at a depolymerization temperature, the melt itself has a microwave-absorbing capability lower than that of the charged (meth)acrylic resin at the depolymerization temperature. In the step 2, an additional (meth)acrylic resin is added to and mixed with the melt having a reduced microwave-absorbing capability and dispersed in the melt, so that the microwaves can be allowed to reach the inside of the melt mixture.

The "additional (meth)acrylic resin" defined as being added in the step 2 in the present invention is added to the melt having a microwave-absorbing capability lower than that of the melt of the charged (meth)acrylic resin, but it is also allowable to add another additional (meth)acrylic resin in a step other than the step 2 in addition to the "additional (meth)acrylic resin" to be added in the step 2. Examples of an aspect in which "another additional (meth)acrylic resin" is added in a step other than the step 2 include an aspect of adding "another additional (meth)acrylic resin" once or in plural times at a timing before obtaining a "melt containing a component having a microwave-absorbing capability lower than that of the charged (meth)acrylic resin at a depolymerization temperature" in the step 1.

A specific aspect of the additional (meth)acrylic resin is preferably a plastic material containing a (meth)acrylic resin, and more preferably a waste plastic material containing a (meth)acrylic resin.

The type of the additional (meth)acrylic resin, the content ratio of the constituent unit derived from the (meth)acrylic monomer, the type of the other monomer, and the weight average molecular weight can be selected from the examples described for the charged (meth)acrylic resin. The blending ratio of the (meth)acrylic resin in the plastic material containing the additional (meth)acrylic resin and the additive component that may be contained in addition to the resin can also be selected from the examples described for the plastic material containing the charged (meth)acrylic resin. The additional (meth)acrylic resin or the plastic material containing the same may be the same as or different from the charged (meth)acrylic resin or the plastic material containing the same.

Specific properties of the additional (meth)acrylic resin may be solid or molten.

The additional (meth)acrylic resin preferably has no thermal history of being provided at a depolymerization temperature from the viewpoint of further suppressing the heterogeneity of the depolymerization system of the (meth) acrylic resin and further efficiently progressing depolymerization in the entire melt. That is, from this viewpoint, it is preferable that the additional (meth)acrylic resin that has been once provided to the depolymerization system is not input again, but the additional (meth)acrylic resin that has not been provided to the depolymerization system is newly input.

Specific examples of the timing of adding the additional (meth)acrylic resin and the added amount (per one time) thereof include adding the additional (meth)acrylic resin in an amount corresponding to a decrease amount at a timing when the amount is decreased by preferably 20 parts by weight or less, more preferably 1 to 20 parts by weight, still more preferably 2 to 18 parts by weight, even more preferably 3 to 15 parts by weight per 100 parts by weight of the charged amount of the charged (meth)acrylic resin.

More specifically, when the charged amount of the charged (meth)acrylic resin is 1 kg or more and less than 50 kg, it is preferable to replenish an additional (meth)acrylic resin in an amount corresponding to a decrease amount at a timing when the amount is decreased by 1 to 15 parts by weight, preferably 3 to 15 parts by weight from 100 parts by weight of the charged amount: when the charged amount of the charged (meth)acrylic resin is 50 kg or more and less than 80 kg, it is preferable to replenish an additional (meth)acrylic resin in an amount corresponding to a decrease amount at a timing when the amount is decreased by 1 to 5 parts by weight, preferably 2.5 to 5 parts by weight from 100 parts by weight of the charged amount; when the charged amount of the charged (meth)acrylic resin is 80 kg or more and less than 400 kg, it is preferable to replenish an additional (meth)acrylic resin in an amount corresponding to a decrease amount at a timing when the amount is decreased by 1 to 4 parts by weight, preferably 2 to 4 parts by weight, more preferably 3 to 4 parts by weight from 100 parts by weight of the charged amount; and when the charged amount of the charged (meth)acrylic resin is 400 kg or more, it is preferable to replenish an additional (meth)acrylic resin in an amount corresponding to a decrease amount at a timing when the amount is decreased by 1 to 3 parts by weight, preferably 1.5 to 3 parts by weight from 100 parts by weight of the charged amount.

The step 2 can be carried out without or with irradiation of microwaves, but can be preferably carried out with irradiation of microwaves from the viewpoint of avoiding complication of control in terms of production method.

The temperature in the step 2 may be at least a temperature at which the additional (meth)acrylic resin is melted, or may be a temperature at which depolymerization described in the step 1 can proceed. From the viewpoint of avoiding complication of control in terms of production method, the same temperature condition as in the step 1 can be set. The temperature control can be performed by microwave irradiation.

The mixing method in the step 2 is not particularly limited, and examples thereof include a method of mixing with a stirrer, a method of rotating a container itself containing a melt mixture, and a method of combining both of these methods. The degree of mixing may be a degree to which the composition of the melt mixture becomes uniform, that is, a degree to which the additional (meth)acrylic resin is uniformly dispersed in the melt mixture.

4. Step 3

In the step 3, the melt mixture obtained in the step 2 is irradiated with microwaves and mixed to obtain a (meth) acrylic monomer.

In the step 3, the phrase "irradiating with microwaves and mixing" includes an aspect of mixing while irradiating with microwaves and an aspect of mixing after irradiating with microwaves.

It is considered that in the melt mixture obtained in the step 2, an additional (meth)acrylic resin is dispersed in the melt in a state where local microwave absorption at the surface of the melt mixture is suppressed and microwaves can reach the inside, so that the depolymerization reaction can proceed in the entire melt. For the additional (meth) acrylic resin, depolymerization proceeds with a time lag behind the charged (meth)acrylic resin. Since the step 3 is performed under mixing, occurrence of a locally excessively heated area is also suppressed, so that an undesirable by-product in the recovered monomer can be reduced.

As the microwave irradiation output in the step 3, an output capable of heating to a temperature at which the depolymerization can proceed is appropriately selected. The temperature at which the depolymerization proceeds in the step 3 is, for example, 280° C. or higher, specifically, 300 to 390° C., preferably 320 to 390° C.

From the viewpoint of further improving the recovery rate of the (meth)acrylic monomer, the temperature at which the depolymerization proceeds in the step 3 is preferably 325 to 390° C., more preferably 330 to 390° C., still more preferably 335 to 390° C., even more preferably 340 to 390° C., still even more preferably 345 to 390° C., and particularly preferably 350 to 390° C.

On the other hand, from the viewpoint of further improving the purity of a desired (meth)acrylic monomer in the recovered monomer liquid, the temperature at which the depolymerization proceeds in the step 3 is preferably 320 to 380° C., more preferably 320 to 370° C., still more preferably 320 to 360° C., even more preferably 320 to 355° C., still even more preferably 320 to 345° C., particularly preferably 320 to 342° C., and most preferably 320 to 340° C. The improvement in the purity of the desired (meth) acrylic monomer in the recovered monomer liquid can also be confirmed by an increase in the weight ratio of the (meth)acrylic monomer in the recovered monomer liquid and/or a decrease in the amount of trace components that may not be easily reflected in the weight ratio. Examples of the trace components include a coloring component that can be confirmed visually or by saturation measurement, and/or methyl isobutyrate that can be confirmed by chromatography.

From the viewpoint of avoiding complication of control in terms of production method, the temperature at which the depolymerization proceeds in the step 3 can be set to the same temperature condition as in the step 1 and/or the step 2. The temperature control can be performed by microwave irradiation.

A specific irradiation output of the microwaves to the depolymerization system in the step 3 may be appropriately set according to the set temperature, the scale of the depolymerization system, and the like, and an effective output (a value obtained by subtracting a reflected wave (KW) from an incident wave (KW)) is, for example, 1 KW or more, preferably 1.2 kW or more, and more preferably 1.5 KW or more. The upper limit of the irradiation output (effective output) is not particularly limited, and is, for example, 200 kW or less.

The frequency of the microwaves applied to the depolymerization system in the step 2 is not particularly limited, and is, for example, 0.8 to 6 GHZ. From the viewpoint of making it easier for microwaves to reach the inside of the melt mixture, the frequency is preferably 0.8 to 2.5 GHZ, more preferably 0.8 to 1.5 GHZ, and still more preferably 0.8 to 1 GHz or 0.9 to 0.95 GHZ. In the production method of the present invention, since the microwaves can reach the inside of the melt mixture, the microwaves can reach the inside of the melt mixture even when microwaves having a frequency of more than 2.5 GHz and 6 GHz or less or more than 1.5 GHZ and 6 GHz or less, particularly 4 to 6 GHZ, which is inherently not advantageous in terms of deep penetration, are used.

The mixing method in the step 3 is not particularly limited, and examples thereof include a method of mixing with a stirring blade, a method of rotating a container itself containing a melt mixture, and a method of combining both of these methods. The degree of mixing may be a degree to which the composition of the melt mixture becomes uniform.

5. Repetition of Step 2 and Step 3

In an embodiment in which the step 2 and the step 3 are repeated, it is possible to continuously update a state where the melt mixture containing the additional (meth)acrylic resin is dispersed in the melt in a state where local microwave absorption is suppressed and microwaves can reach the inside. That is, in the embodiment in which the step 2 and the step 3 are repeated, since depolymerization that makes it possible for the microwaves to reach uniformly and efficiently the system interior can be maintained, metabolism of an object to be depolymerized occurs efficiently throughout the entire melt, and efficient depolymerization becomes possible even in the case of a large-scale depolymerization system.

In the embodiment in which the step 2 and the step 3 are repeated, the timing of the step 2 for adding the additional (meth)acrylic resin again is not particularly limited.

For example, as the timing of the step 2 for adding an additional (meth)acrylic resin again, it is possible to add x parts by weight of an additional (meth)acrylic resin again per 100 parts by weight of the charged amount of the charged (meth)acrylic resin as the (n+1)-th step 2 at the timing when the amount of monomers corresponding to the additional (meth)acrylic resin added in the preceding step 2 is recovered, specifically, in the case of adding x parts by weight of an additional (meth)acrylic resin per 100 parts by weight of the charged amount of the charged (meth)acrylic resin in the n-th step 2, at the timing when the monomer is liquefied and recovered in a weight approximately corresponding to x parts by weight.

For example, from the viewpoint of improving the accuracy of the temperature control in the container and making the decomposition easier to proceed at a desired depolymerization temperature, as the timing of the step 2 for adding an additional (meth)acrylic resin again and the additional added amount, when the total amount of the (meth)acrylic resin in the container at the time of adding the additional (meth) acrylic resin at the previous time is designated as 100 parts by weight, it is preferable to replenish an additional (meth) acrylic resin in an amount corresponding to a decrease amount at a timing when the amount is decreased by 1 to 20 parts by weight from 100 parts by weight of the total amount. More specifically, when the total amount of the (meth)acrylic resin in the container at the time of adding the additional (meth)acrylic resin at the previous time is 1 kg or more and less than 50 kg, it is preferable to replenish an additional (meth)acrylic resin in an amount corresponding to a decrease amount at a timing when the amount is decreased by 1 to 15 parts by weight from 100 parts by weight of the total amount; when the total amount of the (meth)acrylic resin in the container at the time of adding the additional (meth)acrylic resin at the previous time is 50 kg or more and less than 80 kg, it is preferable to replenish an additional (meth)acrylic resin in an amount corresponding to a decrease amount at a timing when the amount is decreased by 1 to 5 parts by weight from 100 parts by weight of the total amount: when the total amount of the (meth)acrylic resin in the container at the time of adding the additional (meth)acrylic resin at the previous time is 80 kg or more and less than 400 kg, it is preferable to replenish an additional (meth)acrylic resin in an amount corresponding to a decrease amount at a timing when the amount is decreased by 1 to 4 parts by weight from 100 parts by weight of the total amount; and when the total amount of the (meth)acrylic resin in the container at the time of adding the additional (meth)acrylic resin at the previous time is 400 kg or more, it is preferable to replenish an additional (meth)acrylic resin in an amount corresponding to a decrease amount at a timing when the amount is decreased by 1 to 3 parts by weight from 100 parts by weight of the total amount.

6. (Meth)Acrylic Monomer Production Device

The configuration of a device that can be used in the method for producing a (meth)acrylic monomer of the present invention is not particularly limited as long as the device has a configuration that enables execution of the steps 1 to 3.

An example of the device that can be used in the method for producing a (meth)acrylic monomer of the present invention is illustrated in FIG. 1. The device illustrated in FIG. 1 includes a container 10 providing a field for a depolymerization reaction: a stirring device 20 for stirring a reaction melt inside the container 10 with stirring blades 211 and 212; a waveguide 30 provided to communicate with the inside of the container 10, sealed by an airtight window 31, and configured to allow microwaves to enter in an R1 direction: a container 40 provided to communicate with the inside of the container 10 and configured to accommodate a plastic material to be additionally added into the container 10 (in an R2 direction); a thermometer 50 for measuring the temperature of the reaction melt in the container 10; a cooling device 60 provided to communicate with the inside of the container 10 and configured to cool the monomer vaporized in the container 10 via a flexible hose 61 (specifically, employing a spiral capacitor and setting a chiller set temperature to 0° C.; and a container 70 in which the liquefied monomer cooled by the cooling device 60 is recovered. In the example of FIG. 1, the bottom of the container 10 has a round bottom shape (a dish shape having a curved shape protruding in the depth direction), and the stirring blades 211 and 212 having paddle shapes on both sides (provided that, the paddle on one side and the paddle on the other side are provided such that both the plane directions are parallel to the rotation axis direction in the stirring blade 211, and the plane directions are orthogonal to each other in the stirring blade 212) are provided at different heights in the vertical direction (the vertical direction in FIG. 1), and are provided so as to be orthogonal to each other as viewed in the vertical direction. The lower stirring blade 211 has a shape along the shape of the bottom inner wall as viewed in the horizontal direction to enable efficient stirring, while the upper stirring blade 211 has an arbitrary shape (for example, a rectangular flat plate shape).

Figure 2:
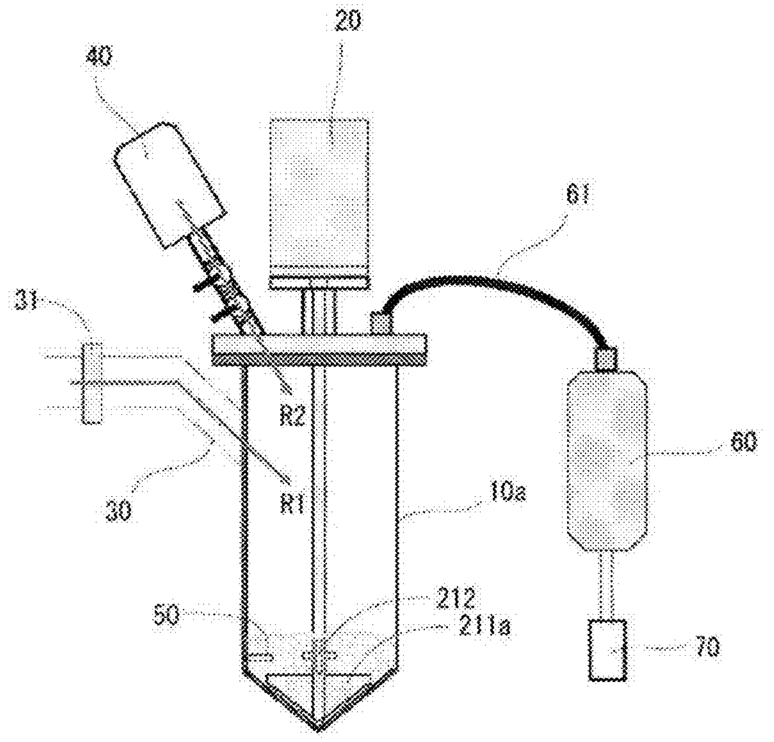
FIG. 2 is a schematic view of another example of a device used in a method for producing a (meth)acrylic monomer of the present invention.

Another example of a device that can be used in the method for producing a (meth)acrylic monomer of the present invention is illustrated in FIG. 2. The device illustrated in FIG. 2 differs from the device illustrated in FIG. 1 in at least shapes of a container 10*a* and a stirring blade 211*a*. The container 10*a* has a bottom whose side wall has an inverted conical shape. Since the container 10*a* has such a bottom shape, electric charges are collected at the bottom (tip) and the electric field strength is increased in the vicinity thereof as compared with the container 10 in the device of FIG. 1, so that microwaves can easily penetrate into a deeper portion and a more uniform reaction can be performed.

EXAMPLES

Hereinafter, the present invention will be more specifically described by means of Examples and Comparative Examples; however, the present invention is not limited thereto.

Example 1

(1) Plastic Material

Polymethyl methacrylate (hereinafter, also referred to as PMMA) was used as the plastic material containing a (meth)acrylic resin to be subjected to depolymerization. This PMMA was a polymer obtained by polymerizing methyl methacrylate (MMA) and methyl acrylate (MA) at MMA: MA=98:2 (weight ratio), and had a weight average molecular weight of 114,190 (measured in terms of tetrahydrofuran as a developing solvent and standard polystyrene by GPC method). This plastic material is made of 100% of PMMA. This plastic material was used as a charged (meth) acrylic resin and an additional (meth)acrylic resin.

(2) Monomer Production Device

A schematic view of a device used for monomer production from a plastic material is illustrated in FIG. 1. The device includes a container 10 providing a field for a depolymerization reaction: a stirring device 20 for stirring a reaction melt inside the container 10 with stirring blades 211 and 212: a waveguide 30 provided to communicate with the inside of the container 10, sealed by an airtight window 31, and configured to allow microwaves to enter in an R1 direction: a container 40 provided to communicate with the inside of the container 10 and configured to accommodate a plastic material to be additionally added into the container 10 (in an R2 direction); a thermometer 50 for measuring the temperature of the reaction melt in the container 10; a cooling device 60 provided to communicate with the inside of the container 10 and configured to cool the monomer vaporized in the container 10 via a flexible hose 61 (specifically, employing a spiral capacitor and setting a chiller set temperature to 0° C.); and a container 70 in which the liquefied monomer cooled by the cooling device 60 is recovered. The bottom of the container 10 has a round bottom shape (a dish shape having a curved shape protruding in the depth direction), and the stirring blades 211 and 212 having paddle shapes on both sides (provided that, the paddle on one side and the paddle on the other side are provided such that both the plane directions are parallel to the rotation axis direction in the stirring blade 211, and the plane directions are orthogonal to each other in the stirring blade 212) are provided at different heights in the vertical direction (the vertical direction in FIG. 1), and are provided so as to be orthogonal to each other as viewed in the vertical direction. The paddle of the lower stirring blade 211 has a shape along the shape of the bottom inner wall as viewed in the horizontal direction, and the paddle of the upper stirring blade 211 has a rectangular flat plate shape.

(3) Operation Procedure

Into the empty container 10, 2.8 kg of PMMA (charged PMMA at the first time) was input, microwaves (microwaves with a frequency of 2.45 GHz; the same applies hereinafter) generated by a microwave oscillator (not illustrated) were incident to PMMA in the container 10 along the waveguide 30 while PMMA was stirring by the stirring device 20, and PMMA was brought into a molten state. While the temperature was measured by the thermometer 50, stirring and microwave irradiation were continued, and the temperature was raised to 340° C. While stirring and microwave irradiation were continued, 0.4 kg of PMMA (charged PMMA at the second time) was added from the container 40 into the container 10. The monomer gas generated in the container 10 was cooled and liquefied by the cooling device 60 via the flexible hose 61, and collected in the container 70. While stirring and microwave irradiation were continued, an operation of adding PMMA (additional PMMA) in an amount of about 0.4 kg from the container 40 was repeated every time the weight of the monomer recovered in the container 70 increased by about 0.4 kg. The monomer recovered in the container 70 was taken out (fractionated) for every about 0.4 kg at the timing of adding additional PMMA, subjected to analysis in (5) described below, and then pooled. The operation of adding additional PMMA was performed at a frequency of approximately once every 10 minutes and continued until the time point of about 300 minutes from the melting of the charged PMMA. The total added amount of the additional PMMA was 11.2 kg. Stirring was also continued throughout the irradiation with microwaves, so that the temperature of the reaction melt in the container 10 was kept uniform and the microwaves were allowed to easily reach the inside of the reaction melt. During depolymerization, the effective output of the microwaves was 1.5 to 2.3 KW (average 1.7 kW). Until the time point of about 300 minutes from the melting of the charged PMMA, the addition of additional PMMA had a substantially constant frequency of approximately once every 10 minutes, and thus favorable reaction efficiency was maintained throughout.

(4) Analysis of Decomposition Rate

When the total weight of the charged PMMA and the total amount of the additional PMMA was designated as A (g), and the residue weight in the container 10 was designated as R (g), the decomposition rate (%), that is, (A−R)/R×100 was calculated. The decomposition rate according to this Example was 80.4%.

(5) Analysis of Recovered Product

The monomer liquid recovered in the container 70 was diluted 100 times with an acetone solvent so as to have a concentration of 1.0 wt %, the obtained diluted solution was provided to an absolute calibration curve method by a gas chromatograph (GC-FID, GC-2010 manufactured by SHIMADZU CORPORATION), and the content of the methacrylic monomer (methyl methacrylate: MMA) in the recovered monomer liquid was measured. Of the content of MMA in the monomer liquid recovered in the container 70, the content of MMA in the monomer liquid recovered first (fractionated) was 99.19 wt %. As the decomposition proceeded, the content of MMA in the monomer liquid recovered (fractionated) in the container 70 decreased, and the content of MMA in the monomer liquid recovered (fractionated) in the container 70 at the time when the decomposition rate was 80.4% was 96.35 wt %.

In the GC analysis using the diluted solution described above, the area value of the peak of methyl isobutyrate (MIBA), which is one of the by-products in the monomer liquid recovered in the container 70, was read as the content of MIBA. Of the content of MIBA in the monomer liquid recovered in the container 70, the content of MIBA in the monomer liquid recovered first (fractionated) was 625 in terms of the area value of the peak. As the decomposition proceeded, the content of MIBA in the monomer liquid recovered (fractionated) in the container 70 increased, and the content of MIBA in the monomer liquid recovered (fractionated) in the container 70 at the time when the decomposition rate was 80.4% was 1,184 in terms of the area value of the peak.

The residue (0.40 g) obtained by performing depolymerization to a decomposition rate of 80.4% was subjected to the following measurement conditions, and a real part e' of complex permittivity, an imaginary part e" of complex permittivity, and the power half-reduction depth of microwaves derived therefrom were calculated. The results are shown in Table 1. In Table 1, also for the charged PMMA, the results measured under the same conditions are shown in comparison. The weight average molecular weight of the residue was 27,263.

(Measurement Conditions)

Equipment used: Cavity resonator (Ryowa Electronics Co., Ltd.)

Frequency: 915 MHZ

Measurement temperature: 340° C.

Quartz tube: f 10 mm×8 mm $N_2$: 100 mL/min

TABLE 1

| | e' | e" | Power half-reduction depth (m) of microwaves |
|---|---|---|---|
| Charged PMMA | 1.8 | 0.35 | 0.14 |
| Residue | 1.8 | 0.15 | 0.32 |

As shown in Table 1, it was confirmed that in the residual component generated by depolymerization, the imaginary part e" of complex permittivity was lower than that of the charged PMMA, and the power half-reduction depth of microwaves was deeper. From this point, it can be reasonably inferred that, from the timing when an additional PMMA among the additional PMMAs repeatedly added to the depolymerization system was added, the microwave-absorbing capability of the melt itself was reduced by the melt accumulating such a residual component having a low microwave-absorbing capability in the melt, and this makes it possible for the microwaves to penetrate into the melt, so that the heterogeneity of the depolymerization system is suppressed, and efficient depolymerization can be performed.

Example 2

The same material and device as in Example 1 were used, the same amount of charged PMMA as in Example 1 was charged in the same manner, and the same operation as in Example 1 was performed except that the heating temperature by microwaves (frequency: 2.45 GHz) was set to 350° C., the effective output of microwaves during depolymerization was set to 2.1 to 2.5 KW (average: 2.2 kW), the operation of adding additional PMMA (0.4 kg per one time) was performed at a frequency of approximately once every 8 minutes and continued until the time point of about 250 minutes from the melting of the charged PMMA, and the total added amount of the additional PMMA was set to 12.8 kg. The decomposition rate and the recovered product were analyzed in the same manner as in Example 1. The temperature of the reaction melt in the container 10 was kept uniform and the microwaves were allowed to easily reach the inside of the reaction melt. Until the time point of about 250 minutes from the melting of the charged PMMA, the addition of additional PMMA had a substantially constant frequency of approximately once every 8 minutes, and thus favorable reaction efficiency was maintained throughout.

The decomposition rate according to this Example was 80.0%. Of the content of MMA in the monomer liquid recovered in the container 70, the content of MMA in the monomer liquid recovered first (fractionated) was 98.81 wt %. As the decomposition proceeded, the content of MMA in the monomer liquid recovered (fractionated) in the container 70 decreased, and the content of MMA in the monomer liquid recovered (fractionated) in the container 70 at the time when the decomposition rate was 80.0% was 95.34 wt %. When all the monomer liquids recovered at the time when the decomposition rate was 80.0% from the monomer liquid recovered first were combined, the average content of MMA was 97.26 wt %.

Of the content of MIBA in the monomer liquid recovered in the container 70, the content of MIBA in the monomer liquid recovered first (fractionated) was 672. As the decomposition proceeded, the content of MIBA in the monomer liquid recovered (fractionated) in the container 70 increased, and the content of MIBA in the monomer liquid recovered (fractionated) in the container 70 at the time when the decomposition rate was 80.0% was 1,475. When all the monomer liquids recovered at the time when the decomposition rate was 80.0% from the monomer liquid recovered first were combined, the average content of MIBA was 1,063.

Example 3

In Example 2, additional PMMA was continuously added until the time point of about 250 minutes from the melting of the charged PMMA, and then depolymerization was continued until the decomposition rate reached 95.4% without adding additional PMMA while stirring and microwave (frequency: 2.45 GHZ) irradiation were continued. The decomposition rate and the recovered product were analyzed in the same manner as in Example 1.

The content of MMA in the monomer liquid recovered (fractionated) in the container 70 at the time when the decomposition rate according to this Example was 95.4% was 78.28 wt %. When all the monomer liquids recovered at the time when the decomposition rate was 95.4% from the monomer liquid recovered first were combined, the average content of MMA was 96.25 wt %.

The content of MIBA in the monomer liquid recovered (fractionated) in the container 70 at the time when the decomposition rate according to this Example was 95.4% was 24,916. When all the monomer liquids recovered at the time when the decomposition rate was 95.4% from the monomer liquid recovered first were combined, the average content of MIBA was 1778.

Example 4

Into the empty container 10, 50 kg of PMMA (charged PMMA at the first time), which is the same material as in Example 1, was input, microwaves (microwaves with a frequency of 915 MHz) generated by a microwave oscillator (not illustrated) were incident to the PMMA in the container 10 along the waveguide 30 while the PMMA was stirring by the stirring device 20, and the PMMA was brought into a molten state. While the temperature was measured by the thermometer 50, stirring and microwave irradiation were continued, and the temperature was raised to 350° C. While stirring and microwave irradiation were continued, 40 kg of PMMA (charged PMMA at the second time) was added from the container 40 into the container 10, so that the total amount of the charged PMMA was 90 kg (target charged amount). The monomer gas generated in the container 10 was cooled and liquefied by the cooling device 60 via the flexible hose 61, and collected in the container 70. While stirring and microwave irradiation were continued, an operation of adding PMMA (additional PMMA) in an amount of about 3 kg, which corresponds to the decrease amount, from the container 40 was repeated every time the weight of PMMA in the container 70 decreased by about 3 kg. The monomer recovered in the container 70 was taken out (fractionated) every time about 40 kg was accumulated, subjected to analysis in (5) described above, and then pooled. The operation of adding additional PMMA was performed at a frequency of approximately once every 5 minutes and continued until the time point of about 360 minutes from the melting of the charged PMMA. The total added amount of the additional PMMA was 250 kg. Stirring was also continued throughout the irradiation with microwaves, so that the temperature of the reaction melt in the container 10 was kept uniform and the microwaves were allowed to easily reach the inside of the reaction melt. During depolymerization, the effective output of the microwaves was 20 to 24 KW (average 22 KW). Until the time point of about 360 minutes from the melting of the charged PMMA, the addition of additional PMMA had a substantially constant frequency of approximately once every 5 minutes, and thus favorable reaction efficiency was maintained throughout. The decomposition rate and the recovered product were analyzed in the same manner as in Example 1.

The decomposition rate according to this Example was 95.1%, and of the content of MMA in the monomer liquid recovered in the container 70, the content of MMA in the monomer liquid recovered first (fractionated) was 91.67 wt %. As the decomposition proceeded, the content of MMA in the monomer liquid recovered (fractionated) in the container 70 decreased, and the content of MMA in the monomer liquid recovered (fractionated) in the container 70 at the time when the decomposition rate was 95.1% was 89.46 wt %.

Of the content of MIBA in the monomer liquid recovered in the container 70 according to this Example, the content of MIBA in the monomer liquid recovered first (fractionated) was 0.06 wt %. As the decomposition proceeded, the content of MIBA in the monomer liquid recovered (fractionated) in the container 70 increased, and the content of MIBA in the monomer liquid recovered (fractionated) in the container 70 at the time when the decomposition rate was 95.1% was 0.14 wt %.

SUMMARY various conditions and results of Examples 1 to 4 are shown in Table 2 below.

TABLE 2

| | | Example 1 | Example 2 | Example 3 | Example 4 |
|---|---|---|---|---|---|
| Charged amount of charged PMMA | | 2.8 kg + 0.4 kg | 2.8 kg + 0.4 kg | 2.8 kg + 0.4 kg | 50 kg + 40 kg |
| Input amount of additional PMMA/once | | 0.4 kg | 0.4 kg | 0.4 kg | 3 kg |
| Total input amount of additional PMMA | | 11.2 kg | 12.8 kg | 12.8 kg | 250 kg |
| Depolymerization temperature | | 340° C. | 350° C. | 350° C. | 350° C. |
| Depolymerization time | With additional PMMA | 300 minutes | 250 minutes | 250 minutes | 360 minutes |
| | Without additional PMMA | — | — | α minutes (until decomposition rate of 95.4%) | — |
| Decomposition rate (depolymerization time) | | 80.4% (300 minutes) | 80% (250 minutes) | 80% (250 minutes) | 95.1% (360 minutes) |
| Final decomposition rate (depolymerization time) | | 80.4% (300 minutes) | 80% (250 minutes) | 95.4% (250 minutes + α minutes) | 95.1% (360 minutes) |
| MMA (target product) | Initial | 99.19 wt % | 98.81 wt % | 98.81 wt % | 91.67 wt % |
| | Final | 96.35 wt % | 95.34 wt % | 78.28 wt % | 89.46 wt % |
| | Average | no data | 97.26 wt % | 96.25 wt % | no data |
| MIBA (by-product) | Initial | 625 | 672 | 672 | 1110 (0.06 wt %) |
| | Final | 1184 | 1475 | 24916 | 2248 (0.14 wt %) |
| | Average | no data | 1063 | 1778 | no data |

As shown in Examples 1 to 4, a high monomer recovery rate was achieved by depolymerizing PMMA by microwave heating while inputting additional PMMA. As shown in Example 3 in which a depolymerization step of not inputting additional PMMA was further performed as compared with Example 2 in which additional PMMA was constantly input until the end of depolymerization, by adding the depolymerization step of not inputting additional PMMA, the PMMA decomposition proceeded, but the amount of by-products increased. That is, it has been found that by performing PMMA depolymerization by microwave heating while inputting additional PMMA, the heterogeneity of the depolymerization system of PMMA is suppressed and microwaves are easier to reach the system interior efficiently. As a result, generation of by-products can be suppressed, and the yield of a target product can be improved. Since the effect obtained by performing the step for depolymerizing PMMA by microwave heating while inputting additional PMMA is remarkably excellent as described above, as shown when comparing with Example 3, even when the depolymerization step of not inputting additional PMMA is further added, an excellent yield of a target product could be achieved as a whole (although it is not as good as Example 2), and as shown in Example 4, even when the reaction scale was extremely increased, the amount of by-products was extremely suppressed in a quantitative manner relative to the reaction scale, and an excellent yield of a target product could be achieved.

Example 5

The same material as in Example 1 was used, and the same operation as in Example 1 was performed except that the container was changed to a container having a volume of 100 mL, the amount of charged PMMA was set to 10 g, the added amount of additional PMMA was set to 1 g per one time, the number of times of addition was 100 times in total, and the heating temperature for depolymerization by microwaves (frequency: 915 MHz) was changed in the order of 350° C. (time points of 1 to 60 times of addition), 375° C. (time points of 61 to 90 times of addition), and 360° C. (time points of 91 to 100 times of addition). A saturation c* of the monomer liquid recovered (fractionated) in the container 70 was measured at each of time points of 40 times, 50 times, and 60 times of addition; time points of 70 times, 80 times, and 90 times of addition; and time points of 100 times of addition.

The monomer liquid recovered in the container 70 was subjected to measurement by an ultraviolet visible infrared spectrophotometer (V-600 manufactured by JASCO Corporation) using a 1 cm quartz cell, and the chromaticity value (L*a*b*) was measured. The coloring degree of yellow was converted to the saturation c* by the following formula. The larger the value of the saturation c*, the stronger the coloring. The results are shown in Table 3.

$$\text{Saturation } c^* = \{(a^*) + (b^*)^2)\}^{1/2} \quad \text{[Mathematical Formula 1]}$$

TABLE 3

| Time point of fractionating monomer liquid (number of times of addition of additional PMMA) | Depolymerization temperature (° C.) | Saturation (c*) |
|---|---|---|
| 40 | 350 | 0.65 |
| 50 | | 0.66 |
| 60 | | 0.68 |
| 70 | 375 | 3.51 |
| 80 | | 4.56 |
| 90 | | 3.4 |
| 100 | 360 | 1.65 |

As is apparent from Table 3, a significant decrease in saturation was observed in the case of the depolymerization temperature of 360° C. as compared with the case of the depolymerization temperature of 375° C. A decrease in saturation was observed even in the case of 350° C. as compared with the case of 360° C. That is, since it was recognized that the coloring decreased in the order of 375°

C., 360° C., and 350° C., it was recognized that the generation of an auxiliary component related to the coloring was suppressed in this order.

The invention claimed is:

1. A method for producing a (meth)acrylic monomer, the production method comprising:

(a) irradiating a charged (meth)acrylic resin with microwaves and mixing to obtain a melt containing a component having a microwave-absorbing capability lower than a microwave-absorbing capability of the charged (meth)acrylic resin at a depolymerization temperature;

(b) adding an additional (meth)acrylic resin to the melt and mixing to obtain a melt mixture containing the additional (meth)acrylic resin in the melt; and (c) irradiating the melt mixture with microwaves and mixing to obtain a (meth)acrylic monomer.

2. The production method according to claim 1, wherein in (a), a charged amount of the charged (meth)acrylic resin is 2.5 kg or more.

3. The production method according to claim 1, wherein in the (a), a charged amount of the charged (meth)acrylic resin is 80 kg or more.

4. The production method according to claim 1, wherein (b) and (c) are repeated.

5. The production method according to claim 1, wherein in (b), the additional (meth)acrylic resin does not have a thermal history of being provided at a depolymerization temperature.

6. The production method according to claim 1, wherein in (b), an added amount of the additional (meth)acrylic resin is 20 parts by weight or less per 100 parts by weight of the charged amount of the charged (meth)acrylic resin.

7. The production method according to claim 1, wherein in (b), the additional (meth)acrylic resin is added at a timing when the charged amount of the charged (meth)acrylic resin is reduced by 1 to 20 parts by weight from 100 parts by weight of the charged amount of the charged (meth)acrylic resin.

8. The production method according to claim 1, wherein (c) is performed under a temperature condition of 300 to 360° C.

9. The production method according to claim 1, wherein a frequency of the microwaves is 0.8 to 6 GHz.

10. The production method according to claim 1, wherein (a)-(c) are performed in a container having a bottom whose side wall has an inverted conical shape.

* * * * *